United States Patent
Awad et al.

(10) Patent No.: US 9,480,656 B1
(45) Date of Patent: Nov. 1, 2016

(54) METHOD OF PREPARING ROSEMARY NANOPARTICLES AND ENCAPSULATED ROSEMARY NANOPARTICLES

(71) Applicant: KING SAUD UNIVERSITY, Riyadh (SA)

(72) Inventors: Manal Ahmed Gasmelseed Awad, Riyadh (SA); Awatif Ahmed Hendi, Riyadh (SA); Promy Virk, Riyadh (SA); Khalid Mustafa Osman Ortashi, Riyadh (SA); Mai Abdelrahman Elobeid Wagealla, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/868,351

(22) Filed: Sep. 28, 2015

(51) Int. Cl.
*A61K 36/53* (2006.01)
*A61K 9/50* (2006.01)

(52) U.S. Cl.
CPC ........... *A61K 9/5073* (2013.01); *A61K 9/5026* (2013.01); *A61K 9/5036* (2013.01); *A61K 9/5089* (2013.01); *A61K 36/53* (2013.01); *A61K 2236/39* (2013.01)

(58) Field of Classification Search
None
See application file for complete search history.

(56) References Cited

U.S. PATENT DOCUMENTS 8,580,253 B2    11/2013  Rubin-Bejerano et al.
2009/0312402 A1 12/2009  Contag et al.
2011/0021592 A1  1/2011  Magdassi et al.
2012/0202694 A1  8/2012  Dodd et al.
2013/0017239 A1  1/2013  Viladot Petit et al.
2014/0326812 A1 11/2014  Dodd et al.

OTHER PUBLICATIONS

Abdelwahed et al. (2006) International J. of Pharmaceutics 309: 178-188.*
Bilati et al. (2005) Eur. J. Pharma. Sci. 24: 67-75.*
Chin et al. (2011) Carbohydrate Polymers 86: 1817-1819.*
Chorny et al. (2002) J. Controlled Release 83: 389-400.*
Debersac et al. (2001) Food and Chemical Toxicology 39: 907-918.*
Visentin et al. (2012) J. Food Engineering 109: 9-15.*
Bilati et al., "Development of a nanoprecipitation method intened for the entrapment of hydrophilic drup into nanoparticles", Eur. J. of Pharm. Sci., 24, Jan. 2005, pp. 67-75.
Visentin et al., "Precipitation and encapsulation of rosemary antioxidants by supercritical antisolvent process", J. of Food Eng., 2012, 109, 9-15.
Fernandes et al., "Microencapsulation of Rosemary Essential Oil: Characterization of Particles", Drying Technology, 2003, 31, pp. 1245-1254.

* cited by examiner

*Primary Examiner* — Russell Fiebig
(74) *Attorney, Agent, or Firm* — Richard C. Litman (57) ABSTRACT

A method of preparing rosemary nanoparticles includes providing a solution including rosemary extract, spraying the rosemary extract solution into boiling water under ultrasonic conditions to produce a sonicated mixture, and freeze-drying the sonicated mixture to produce rosemary nanoparticles. The rosemary nanoparticles and encapsulated rosemary nanoparticles with polymers can have a particle size of about 69 nm to about 99 nm. The rosemary nanoparticles and encapsulated rosemary nanoparticles with polymers can be prepared without the use of metals.

3 Claims, 10 Drawing Sheets

METHOD OF PREPARING ROSEMARY NANOPARTICLES AND ENCAPSULATED ROSEMARY NANOPARTICLES

BACKGROUND OF THE INVENTION

1. Field of the Invention

The present invention relates to nanoparticles, and particularly to a method of preparing rosemary nanoparticles and encapsulated rosemary nanoparticles.

2. Description of the Related Art

The three metals, lead, mercury and cadmium, and the metalloid arsenic have all caused major human health problems in various parts of the world. There has been an increasing concern about the rapidly rising level of chemicals in the environment, particularly lead, which has well-known hazardous effects. Lead has no known biological role. Its ubiquitous environmental distribution is from production of coal, oil, iron, steel, and batteries, as well as from smelters, solid waste, and tobacco smoke. Lead affects nearly all organ systems including gastrointestinal, hematopoietic, cardiovascular, nervous, immune, reproductive, and renal system. It targets several vital enzymatic reactions of the body by binding with the sulfhydryl and carboxyl groups present in enzymes. Lead has also been reported to facilitate the onset of oxidative stress on account of the generation of reactive oxygen species (ROS).

Arsenic is a naturally occurring element in the earth's crust and can be found in many natural ecosystems. Mining of arsenic containing ores often releases arsenic into the soil. Burning of arsenic containing fossil fuels, volcanic eruptions, and weathering processes also can introduce substantial amounts of arsenic into the environment. The presence of arsenic in natural waters may originate from geochemical reactions, industrial waste discharges or agricultural use of pesticides containing arsenic. Prolonged exposure to arsenic has been linked to numerous health problems due to its toxicity. Health problems associated with arsenic exposure include, for example, hyperkeratosis on palms and/or feet, fatigue symptoms of arsenicosis, and cancer of the bladder, skin and other organs.

Chelation, antioxidant and herbal therapies are three strategies commonly used for treatment of arsenic toxicity. These commonly used treatments, however, fail to provide an effective treatment for arsenicosis.

Thus, a method of preparing rosemary nanoparticles solving the aforementioned problems is desired.

SUMMARY OF THE INVENTION

A method of preparing rosemary nanoparticles or encapsulated rosemary nanoparticles includes providing a solution including rosemary extract, spraying the rosemary extract solution into boiling water under ultrasonic conditions to produce a sonicated mixture, and freeze-drying the sonicated mixture to produce rosemary nanoparticles and encapsulated rosemary nanoparticles with polymers (starch and PVA polymers). The rosemary nanoparticles can have a particle size of about 69 nm to about 99 nm. The rosemary nanoparticles can be prepared without the use of metals.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A method of preparing rosemary nanoparticles includes providing a solution including rosemary extract, spraying the rosemary extract solution into boiling water dropwise, under ultrasonic conditions to produce a sonicated mixture, and freeze-drying the sonicated mixture to produce rosemary nanoparticles. The rosemary nanoparticles can have a particle size of about 69 nm to about 99 nm. The rosemary nanoparticles can be prepared without the use of metals.

The rosemary extract can be prepared from leaves of the rosemary (*Rosmarinus officinalis*) plant in any suitable manner. The extract can be prepared using dichloromethane (DCM), ethanol, and/or other suitable solvents. For example, leaves of rosemary can be crushed to a powder and extracted with dichloromethane. In detail, the rosemary extract solution can be prepared by mixing about 150 mg of rosemary with about 30 mL of dichloromethane. About 1 mL of the rosemary extract solution can be sprayed into 75 mL of boiling water drop wise with a flow rate of 0.2 mL/min for about 5 minutes under ultrasonic conditions. The ultrasonic conditions can include ultrasonic power of 100 W and a frequency of 30 kHz. Ultrasonic conditions can be maintained for about 10 minutes. The sonicated mixture can be stirred at about 200-800 rpm at room temperature for about 20 minutes prior to freeze-drying.

The rosemary nanoparticles can include a nanoparticle composite or encapsulated rosemary nanoparticles with polymers. Encapsulation of rosemary nanoparticles can protect against degradation factors and facilitate solubility of the nanoparticles in their target medium. The encapsulated rosemary nanoparticles or nanoparticle composites can be prepared by nanoprecipitation (Bilati et al. 2005; Zili et al., 2005). The nanoparticle composites can include starch and polyvinyl alcohol (PVA) as carriers. The rosemary nanoparticles can be encapsulated with a starch/PVA blend to provide a nanoparticle composite including a 1:5:5 ratio (w/w/w) of rosemary:starch:PVA. In detail, about 150 mg of rosemary and an appropriate amount of starch can be dissolved in about 50 mL of ethanol. The internal organic phase solution can be injected into about 150 mL of an external aqueous solution including the appropriate amount of PVA. The solution can be homogenized and ethanol can be removed from the solution. The mixture can be freeze-dried to provide a nanoparticle powder, with particle size of about 69 nm.

The rosemary nanoparticles possess potent antioxidant, anti-inflammatory, antitumor and antimicrobial properties. In particular, the rosemary nanoparticles can be an effective antioxidant. Extracts of rosemary have been reported to demonstrate higher antioxidant activity than that found in naturally occurring plants. Further, rosemary extracts produced using a solvent blend have been reported to demonstrate an antioxidant activity of at least 50% that of mixed tocopherols. Also, because of their small size, rosemary nanoparticles are easily accessible in the body and can be transported to different sites through the blood.

The therapeutic efficacy of drugs can be particularly enhanced via targeting using rosemary nanomaterials as carriers. It has been demonstrated that site-specific, targeted delivery of drugs can be facilitated using appropriate carriers such as liposomes, micelles and nanoparticles. Nanoparticles are easily accessible in the body and can be transported to different sites through the blood. One way this can be achieved is by making the particle surface hydrophilic by conjugating it with an amphiphilic polymer made of polyethylene oxide such as polyoxamer and polyoxamine. Nanoparticles can thus evade the reticuloendothelial system (RES) such as liver Kupffer cells and spleen macrophages and can be delivered to the desired site effectively.

Figure 10:
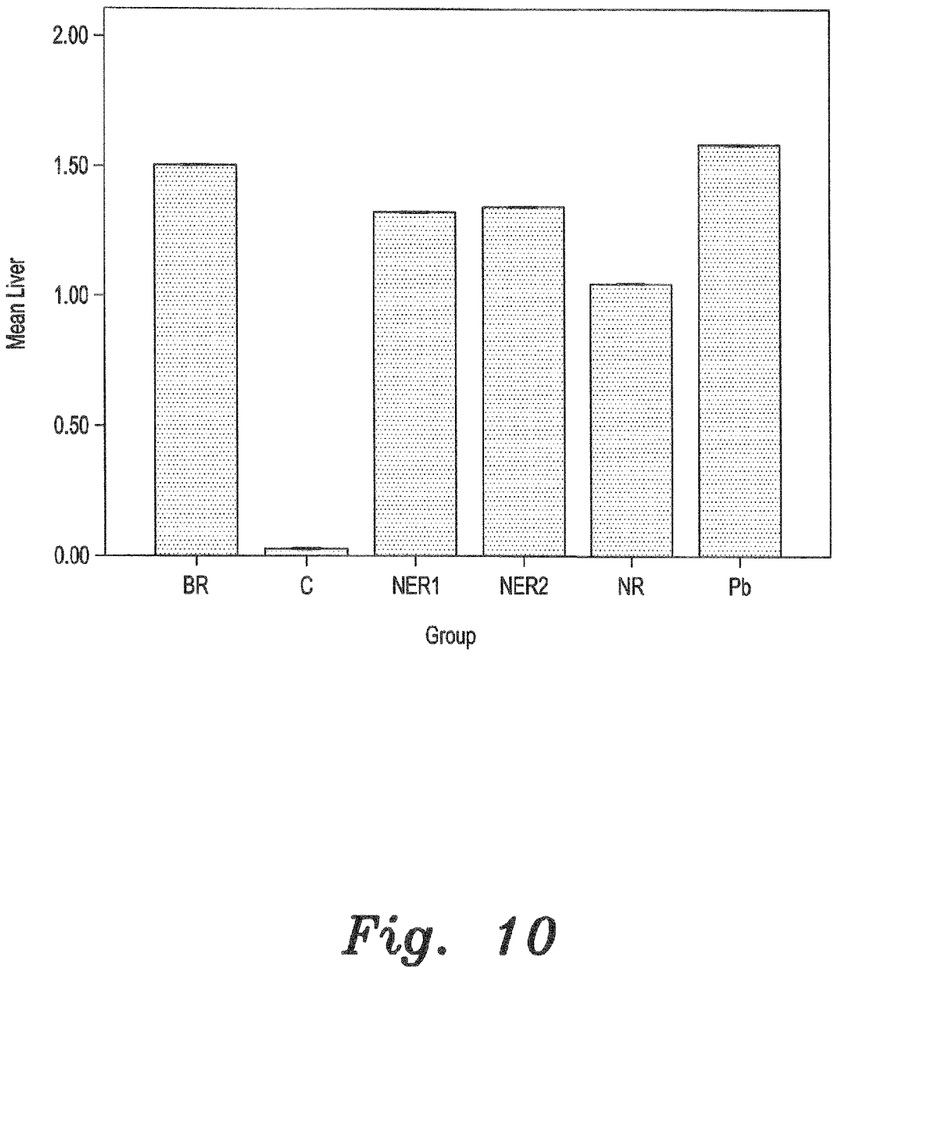
FIG. 10 is a graph showing mean lead concentration in the liver of rats from the experimental groups described herein.
Figure 11:
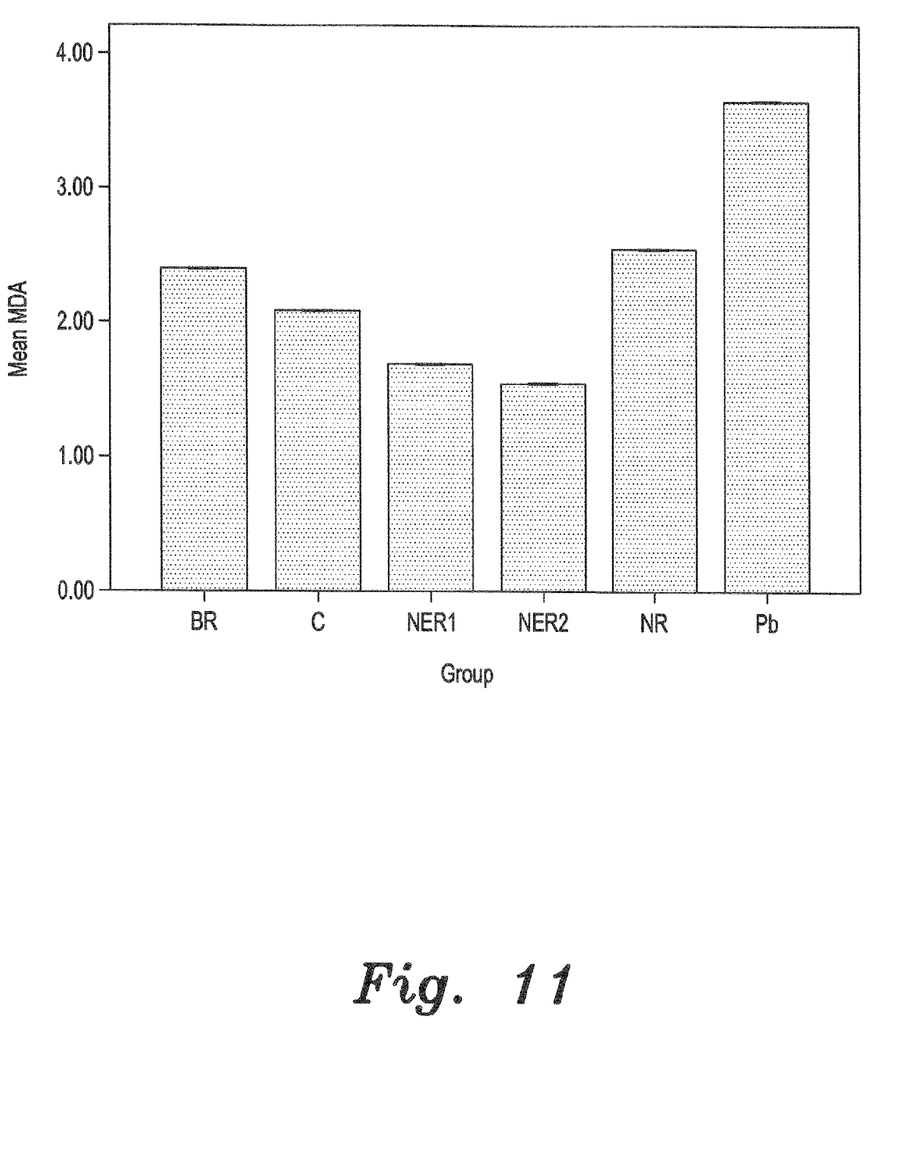
FIG. 11 is a graph showing mean serum MDA levels of rats from the experimental groups described herein.

The rosemary nanoparticles can be used to treat a patient for an illness caused by elevated levels of a heavy metal, such as lead or arsenic, in the body. The rosemary nanoparticles can be used to treat arsenicosis, for example. Studies have shown that exposure to arsenic (As) and lead (Pb) produces oxidative stress, one of the most noted molecular mechanisms for the toxicity of these metals. As discussed in further detail below, the present inventors have found that the rosemary nanoparticles can be used to alleviate oxidative stress. The present inventors have found that treating rat groups exposed to lead with rosemary extract demonstrated reduced bioaccumulation of lead in kidney (FIG. 7), muscle (FIG. 8), brain (FIG. 9), and liver (FIG. 10). However, in comparison to the bulk rosemary treatment, treatment with rosemary nanoparticles proved to be more beneficial overall (FIGS. 7-10). The present inventors further found that the lead exposure induced oxidative stress in the rats and that treatment with rosemary extract significantly reduced serum malondialdehyde (MDA) levels (FIG. 11). However, in comparison with the rosemary extract treatment, treatment with rosemary nanoparticles proved to be more efficacious in reducing the serum MDA levels, thus mitigating oxidative stress (FIG. 11).

The following examples are provided by way of illustration.

Example 1

Figure 1:
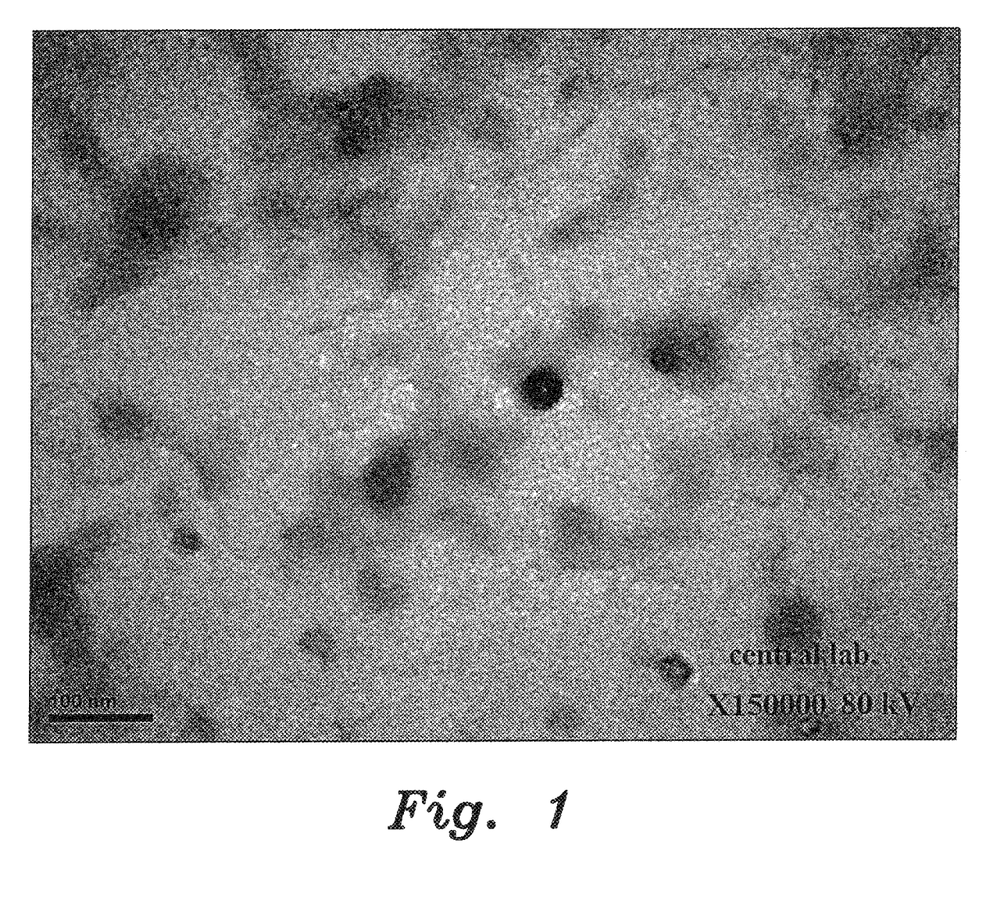
FIG. 1 is a transmission electron microscopy (TEM) image of rosemary nanoparticles of Example 1 prepared according to the present invention.
Figure 2:
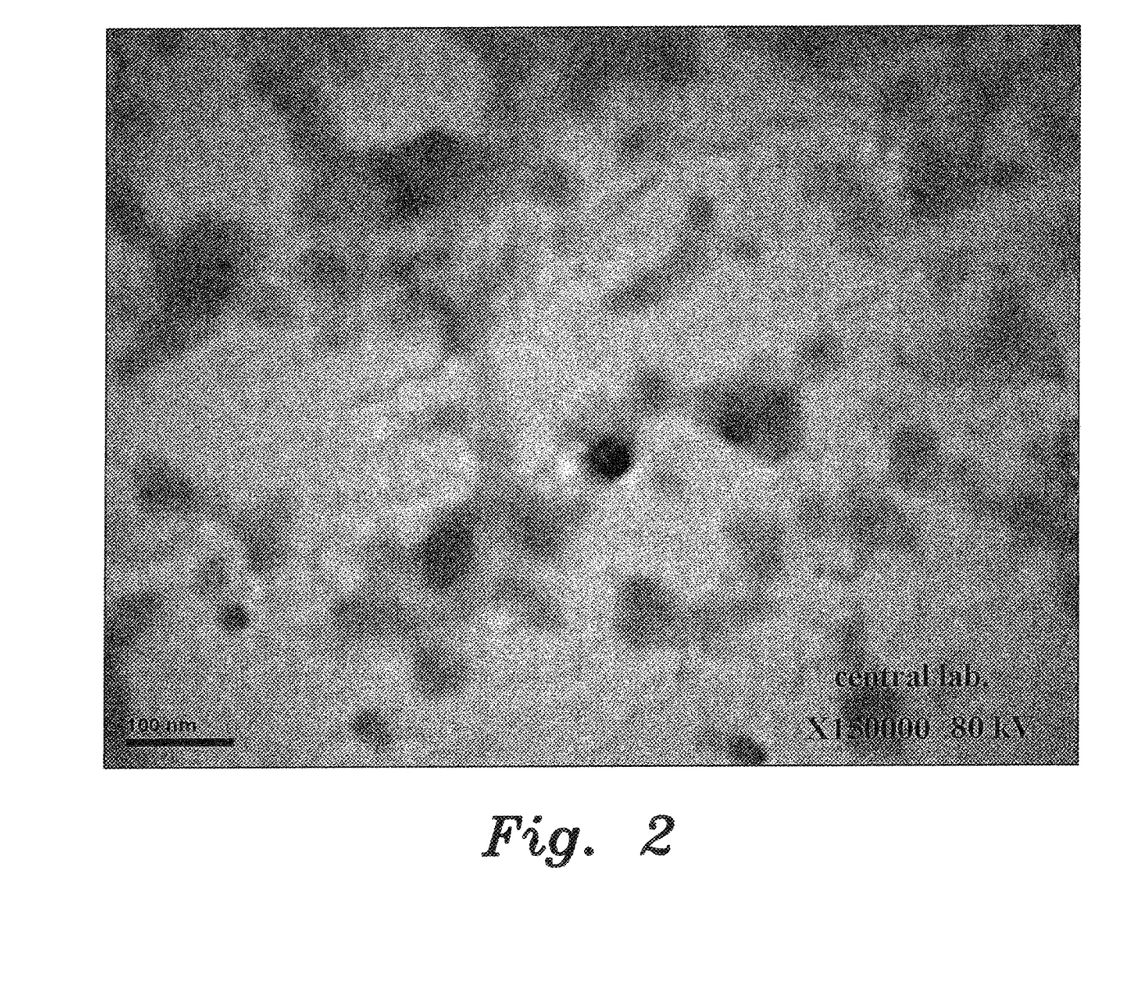
FIG. 2 is a transmission electron microscopy (TEM) image of rosemary nanoparticles of Example 1 prepared according to the present invention.
Figure 5:
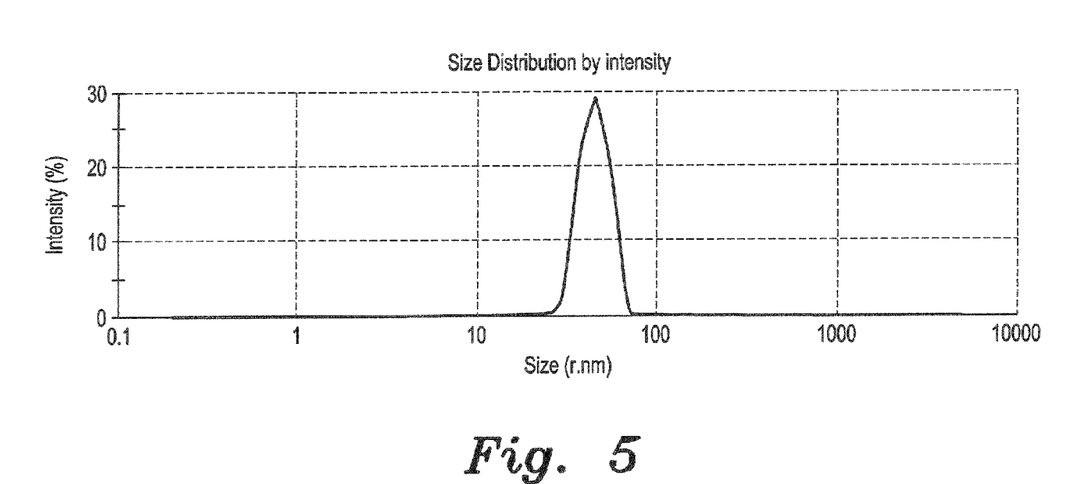
FIG. 5 shows a Zeta sizer graph for measuring the average particle size of the rosemary nanoparticles prepared according to Example 1 according to the present invention.

For preparing rosemary nanoparticles (150 mg) rosemary was taken in dichloromethane (30 mL), and 1 mL of this solution was sprayed into boiling water (75 mL) dropwise with a flow rate of 0.2 mL/min in 5 min under ultrasonic conditions, with an ultrasonic power of 100 W and a frequency of 30 kHz. After sonication for 10 min, the contents was stirred at 200-800 rpm at room temperature for about 20 minutes, then freeze-dried, to obtain rosemary nanoparticles, appearing as greenish powder with a particle size of 99.43 nm. FIGS. 1 and 2 are transmission electron microscopy (TEM) (JEM-1011, JEOL, Japan) images of the rosemary nanoparticles. The rosemary nanoparticles were analyzed using a Zeta sizer (ZEN 3600, MALVERN, United Kingdom). FIG. 5 shows a Zeta sizer graph indicating the average particle size of the rosemary nanoparticles.

Example 2

Figure 3:
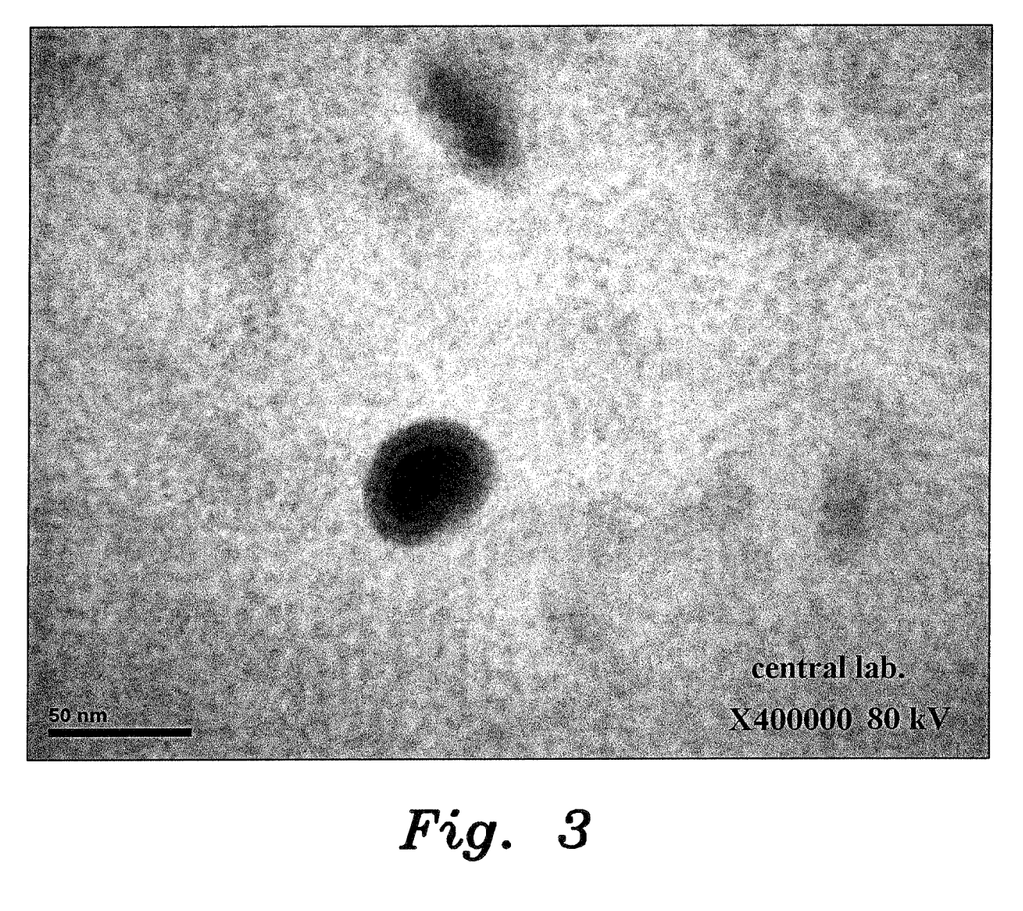
FIG. 3 is a transmission electron microscopy (TEM) image of encapsulated rosemary nanoparticles of Example 2, according to the present invention.
Figure 4:
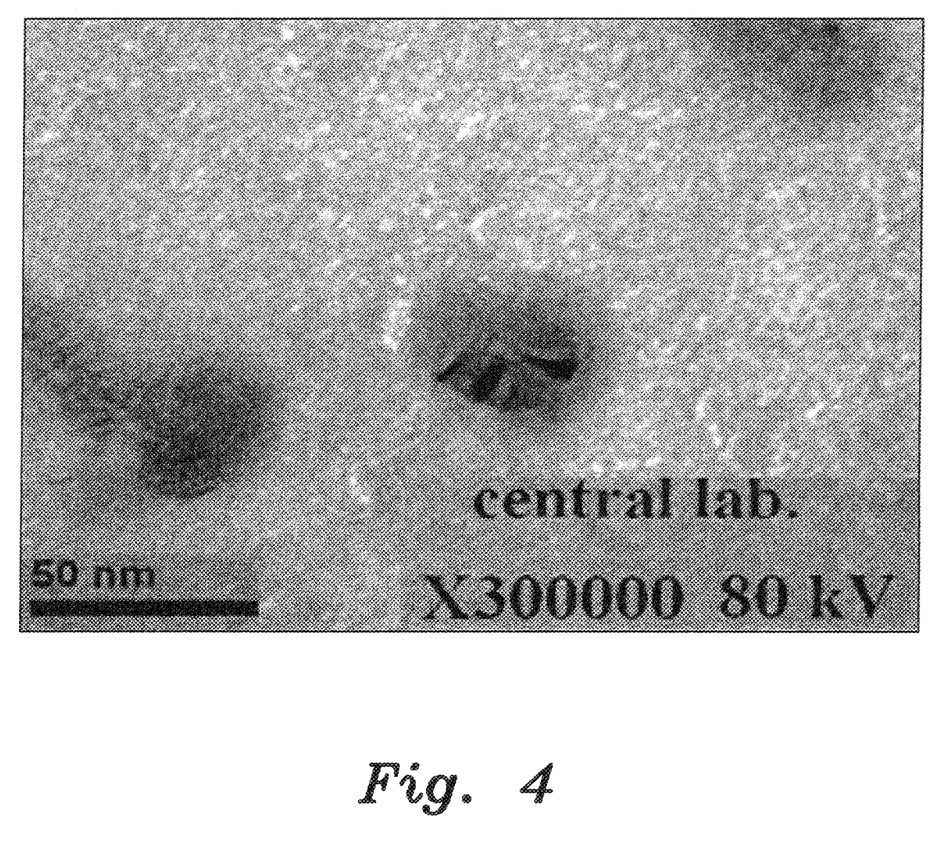
FIG. 4 is a transmission electron microscopy (TEM) image of encapsulated rosemary nanoparticles of Example 2, according to the present invention.
Figure 6:
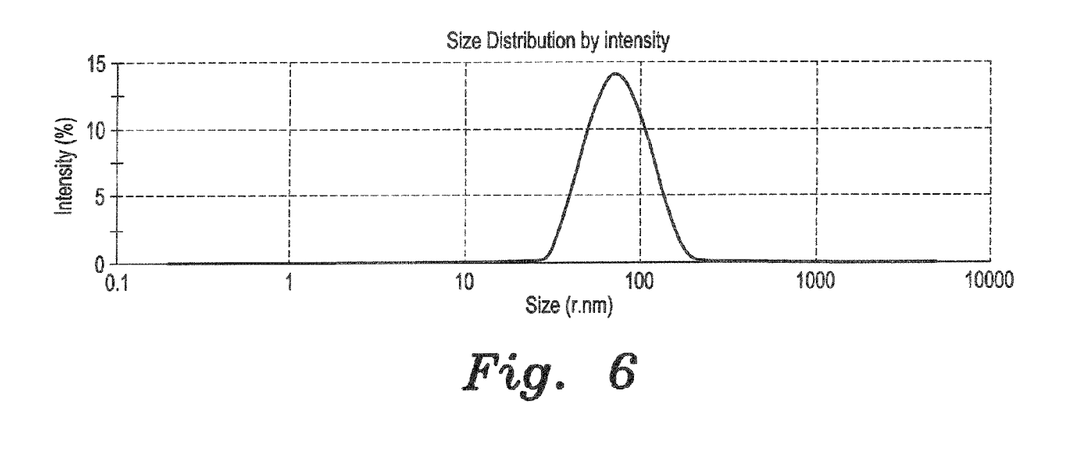
FIG. 6 shows a Zeta sizer graph for measuring the average particle size of the rosemary nanoparticles prepared according to Example 2 according to the present invention.
Figure 7:
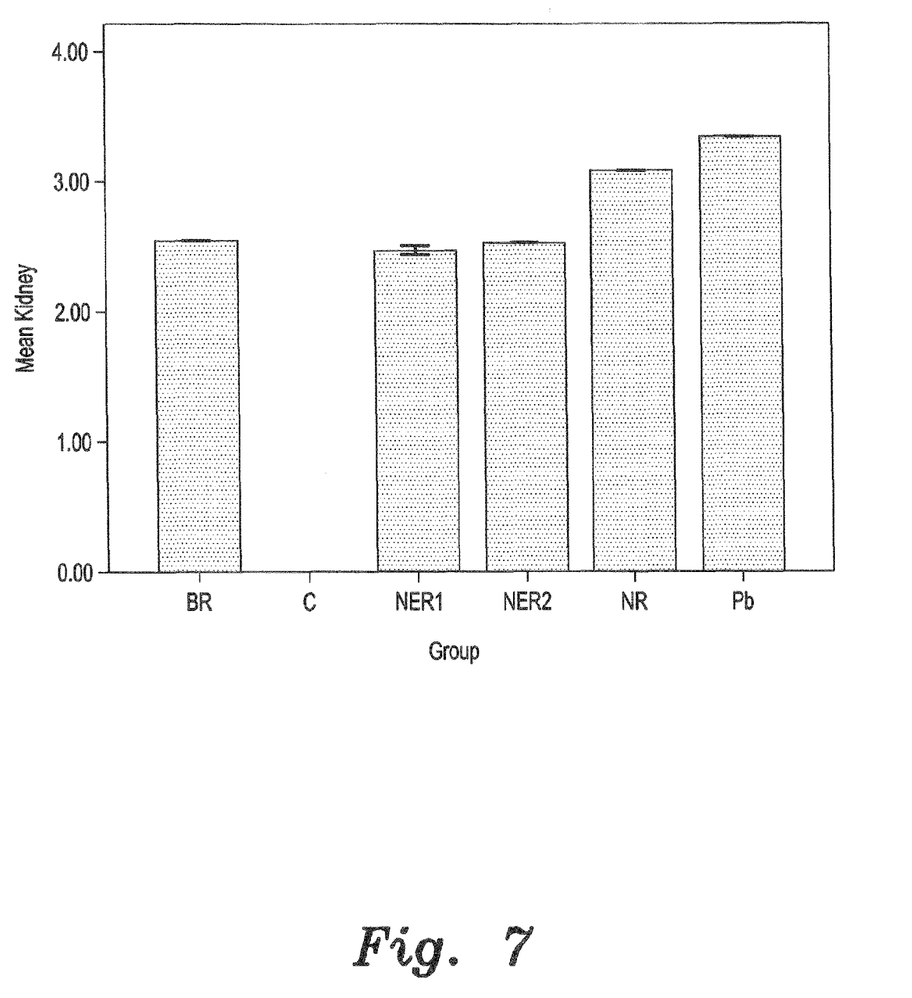
FIG. 7 is a graph showing mean lead concentration in the kidney of rats from the experimental groups described herein.
Figure 8:
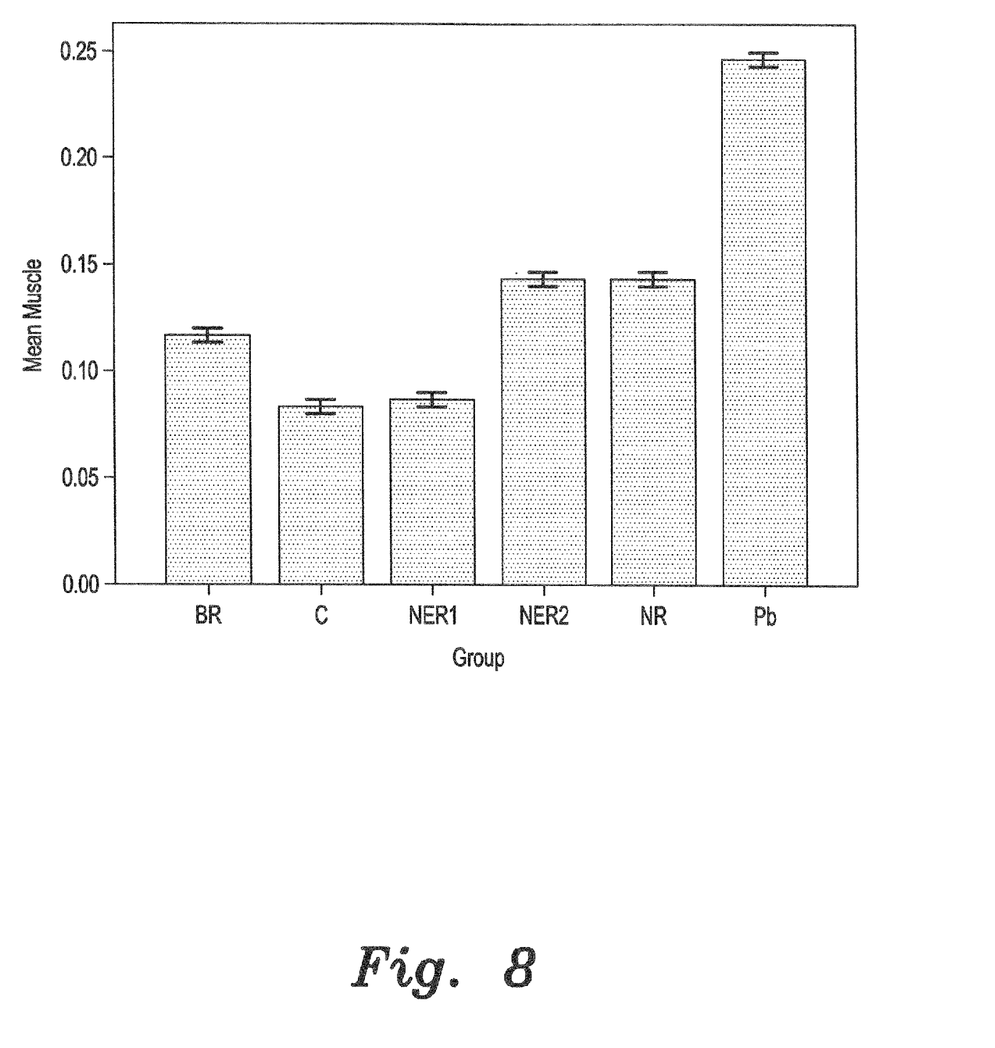
FIG. 8 is a graph showing mean lead concentration in the muscle of rats from the experimental groups described herein.
Figure 9:
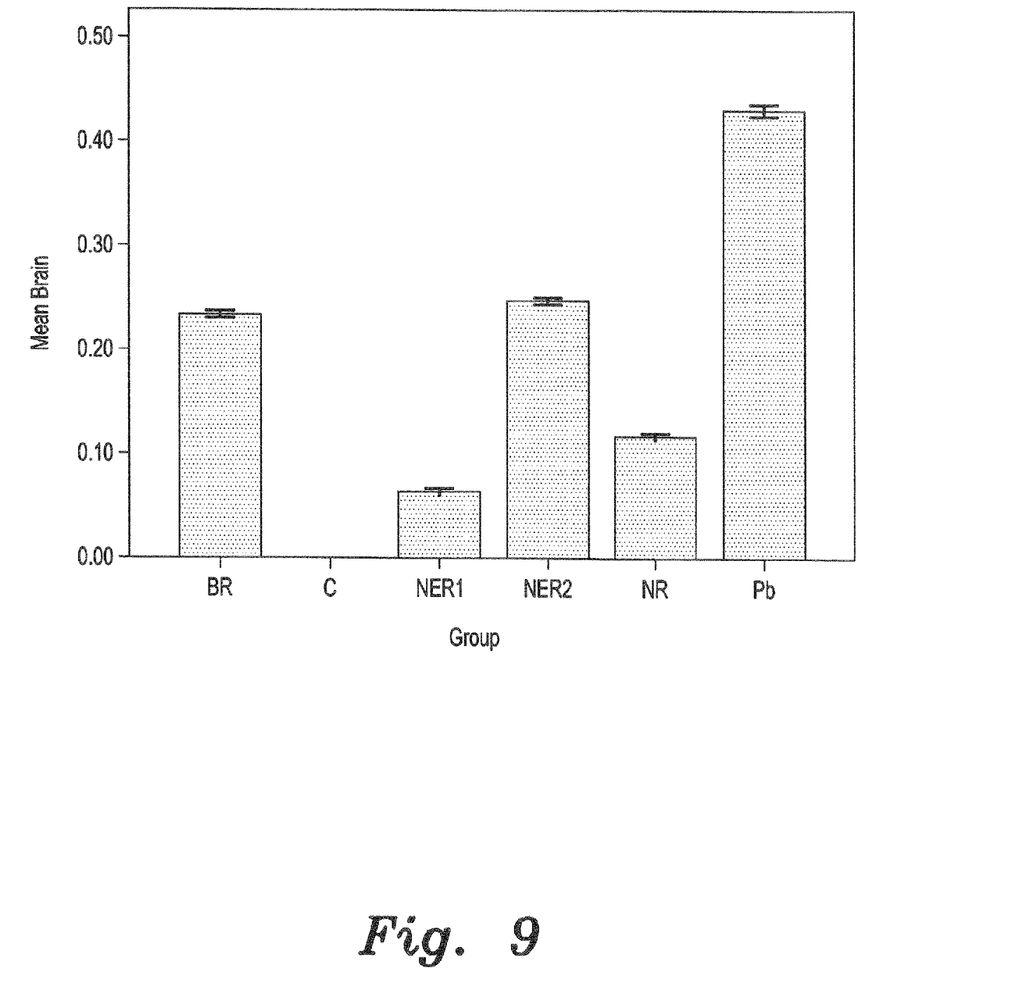
FIG. 9 is a graph showing mean lead concentration in the brain of rats from the experimental groups described herein.

For preparing encapsulated rosemary nanoparticles, a nanoprecipitation technique was used to form encapsulated rosemary nanoparticles with starch and PVA. The ratio of rosemary:starch:PVA was 1:5:5; w/w/w. An amount of 150 mg of rosemary and the appropriate amount of starch (375-750 mg) was dissolved in 50 ml of ethanol. The internal organic phase solution was quickly injected into 150 ml external aqueous solution containing the appropriate amount of PVA (375-750 mg), and then the solution was homogenized at 22,000 rpm for 25 minutes. The ethanol was completely removed, and then freeze-dried to provide nanoparticle powder with a particle size of about 69.373 nm. FIGS. 3 and 4 are transmission electron microscopy (TEM) (JEM-1011, JEOL, Japan) images of the rosemary nanoparticles. The encapsulated rosemary nanoparticles were analyzed using a Zeta sizer (ZEN 3600, MALVERN, United Kingdom). FIG. 6 shows a Zeta sizer graph indicating the average particle size of the rosemary nanoparticles.

Example 3

FIGS. 7-10 show results of data collected from tests on treated and untreated rats exposed to lead. Lead concentration in the kidney, muscle, brain, and liver of rats from the positive control group (Pb) was significantly ($p \leq 0.001$) higher than the control group (C). All groups treated with Rosemary extract did significantly ($p \leq 0.001$) reduce the bioaccumulation of lead in all tissues. However, in comparison to the bulk rosemary treatment (BR), the nanotreatment (1.25-2.5 ppm) proved to be more beneficial. Within the nanotreated groups (NR), (NER1), and (NER2), the group treated with encapsulated nanoparticles of rosemary (NER1) and (NER2) proved to be more efficacious in reducing the lead concentration in kidney, muscle and brain (FIGS. 7-10).

Example 4

FIG. 11 shows results of data collected from tests on treated and untreated rats exposed to lead. The exposure to lead did induce oxidative stress in the rats, which was evident from significantly ($p \leq 0.001$) elevated levels of serum malondialdehyde (MDA) levels in rats from the positive control group (Pb) in comparison to the control group (C). Treatment with rosemary extract did significantly ($p \leq 0.001$) reduce the MDA levels in the serum. However, in comparison to the bulk rosemary treatment (BR), the nanotreatment proved to be more beneficial. Within the nanotreated groups (NR), (NER1), and (NER2), the group treated with encapsulated nanoparticles of rosemary (NER1) and (NER2) proved to be more efficacious in reducing the serum MDA levels and thus mitigating the oxidative stress (FIG. 11).

It is to be understood that the present invention is not limited to the embodiments described above, but encompasses any and all embodiments within the scope of the following claims.

We claim:

1. A method of preparing rosemary nanoparticles, comprising the steps:
    (a) combining about 30 mL dichloromethane (DCM) and about 150 mg rosemary extract to produce a first solution,
    (b) adding the first solution to an aqueous second solution under ultrasonic conditions to produce a sonicated solution,
    (c) stirring the sonicated solution for a sufficient duration to produce a mixture,
    (d) freeze-drying the mixture to produce rosemary nanoparticles having a particle size of about 99 nm.

2. The method according to claim 1, wherein the step of adding the first solution to the second solution comprises spraying about 1 mL of the first solution into about 75 mL of boiling water at a flow rate of about 0.2 mL/min for about 5 minutes under ultrasonic power of 100 W and a frequency of 30 kHz.

3. The method according to claim 2, wherein the mixture is stirred at about 200-800 rpm at room temperature for about 20 minutes prior to freeze-drying.

* * * * *